(12) United States Patent
Yetukuri et al.

(10) Patent No.: US 6,983,638 B2
(45) Date of Patent: Jan. 10, 2006

(54) HEAD RESTRAINT EVALUATOR

(75) Inventors: Nagarjun Yetukuri, Rochester Hills, MI (US); Mladen Humer, Eastpointe, MI (US); Gerald S. Locke, Lake Orion, MI (US); Eric Veine, Madison Heights, MI (US)

(73) Assignee: Lear Corporation, Southfield, MI (US)

( * ) Notice: Subject to any disclaimer, the term of this patent is extended or adjusted under 35 U.S.C. 154(b) by 119 days.

(21) Appl. No.: 10/708,689

(22) Filed: Mar. 18, 2004

(65) Prior Publication Data

US 2005/0204800 A1 Sep. 22, 2005

(51) Int. Cl.
G01M 7/00 (2006.01)

(52) U.S. Cl. ..................... 73/12.04; 73/865.3
(58) Field of Classification Search ............... 73/12.04, 73/12.09, 865.3
See application file for complete search history.

(56) References Cited

U.S. PATENT DOCUMENTS

| | | | | |
|---|---|---|---|---|
| 4,201,078 A | | 5/1980 | Morinaga ....................... 73/12 |
| 5,259,765 A | * | 11/1993 | Richards ..................... 434/274 |
| 5,373,749 A | | 12/1994 | Strand et al. ............... 73/865.3 |
| 5,483,845 A | * | 1/1996 | Stein et al. ................. 73/865.3 |
| 5,641,917 A | | 6/1997 | Hurite et al. ............... 73/865.3 |
| 5,922,937 A | | 7/1999 | Kowalski et al. .......... 73/12.14 |
| 6,023,984 A | | 2/2000 | Mazur et al. ............... 73/865.3 |
| 6,035,728 A | | 3/2000 | Jost ............................ 73/865.3 |
| 6,131,436 A | | 10/2000 | O'Bannon et al. ................ 73/7 |
| 6,381,758 B1 | * | 5/2002 | Roberts et al. ................. 2/421 |
| 6,386,054 B1 | * | 5/2002 | Jones et al. ................. 73/865.3 |
| 6,561,007 B1 | * | 5/2003 | Bock et al. ................. 73/12.01 |
| 6,662,093 B2 | * | 12/2003 | Farmer ........................ 701/45 |
| 6,672,177 B2 | * | 1/2004 | Hutchenreuther et al. . 73/865.3 |
| 2002/0083783 A1 | * | 7/2002 | Ahn .......................... 73/866.4 |
| 2002/0157450 A1 | * | 10/2002 | Hutchenreuther et al. . 73/11.04 |
| 2004/0010398 A1 | * | 1/2004 | Noma et al. ................... 703/1 |

OTHER PUBLICATIONS

Ola Bostrom et al., *A Sled Tests Procedure Proposal to Evaluate the Risk of Neck Injury in Low Speed Rear Impacts Using a New Neck Injury Criterion(NIC)*, 16th ESV Conference, Jun. 1-4, 1998, Windsor, Canada.

Hans Cappon et al., *A New Test Method for the Assessment of Neck Injuries in Rear-End Collisions*, Article, undated.

* cited by examiner

*Primary Examiner*—Max Noori
(74) *Attorney, Agent, or Firm*—Wood, Herron & Evans, L.L.P.

(57) ABSTRACT

A test assembly for evaluating vehicle head restraints comprises a carriage adapted to be coupled to a drive member capable of moving the test assembly, a head restraint coupled to the carriage and a manikin assembly having a head portion and a neck portion with an upper and lower end. The head portion couples to the upper end of the neck portion and the manikin assembly couples to the carriage at the lower end of the neck assembly. The head restraint is positioned adjacent the manikin assembly so that movement of the drive member causes the head portion of the manikin assembly to contact the head restraint. The manikin assembly may further include a load cell and accelerometer for evaluating the effectiveness and performance of a particular head restraint design.

24 Claims, 2 Drawing Sheets

HEAD RESTRAINT EVALUATOR

FIELD OF THE INVENTION

The present invention pertains generally to a vehicle component test device and more particularly to a test assembly for evaluating vehicle head restraints.

BACKGROUND OF THE INVENTION

The automotive industry continually strives to provide safe automobiles and so incorporate a number of safety restraint components in a vehicle that reduce the likelihood of injury in the case of a collision. One such safety restraint component is a head restraint. Such head restraints may be active or passive. It is known in the industry to provide a head restraint generally positioned on the back of the seat occupied by a driver or passenger so that in the event of a collision, such as a rear-impact collision, that tends to throw the head in the rearward direction, the head restraint will support the occupant"s head and limit head motion so as to reduce the likelihood of serious injury.

Motor vehicle components must comply with minimum safety requirements mandated by the federal government or comply with OEM specifications that go beyond the federally mandated requirements. Commonly, the specifications are pursuant to required testing procedures. One such testing procedure is directed toward vehicle seat assemblies, including head restraints. Such vehicle seat assemblies are typically tested in a traditional sled test. In the traditional sled test, the entire seat assembly is securely mounted to the sled and a manikin, having at least a torso and head and neck assembly, is positioned in the seat cushion. The sled is then moved along a rail system in a controllable manner. The sled is typically capable of accelerating and/or decelerating motion that causes the manikin assembly to contact and/or penetrate portions of the seat assembly. The dynamic response of the manikin and manikin/seat assembly interactions are monitored and the data used to determine the performance and effectiveness of the overall seat assembly. A vehicle head restraint is typically evaluated during the testing of the overall seat assembly.

During the developmental stages of vehicle component design, several different designs may be proposed. For instance, it is not uncommon that several different head restraint design concepts may be proposed during the development of a vehicle seat assembly. The proposed head restraint design concepts must then be evaluated or tested to determine the viability of each design and eventually which head restraint design concept will be used for vehicle seat assembly production. As it currently stands, in order to test each proposed head restraint design concept, a seat assembly incorporating the proposed head restraint is tested using the traditional sled test as previously described. Evaluating several proposed head restraint design concepts using a sled test on the overall seat assembly is a costly and time consuming methodology.

There is thus a need for an apparatus and method that can be used during the developmental stages of vehicle component design to evaluate several proposed head restraint design concepts in a more cost effective and time efficient manner.

SUMMARY OF INVENTION

The present invention provides a test assembly for evaluating head restraint design concepts without the need of performing a sled test on the overall seat assembly. The test assembly comprises a carriage adapted to be coupled to a drive member capable of moving the test assembly, a head restraint coupled to the carriage and a manikin assembly comprising a head portion and a neck portion having an upper and lower end. The head portion is coupled to the upper end of the neck portion and the manikin assembly is coupled to the carriage at the lower end of the neck portion. The head restraint is positioned adjacent the manikin assembly so that movement of the drive member causes the head portion of the manikin assembly to contact the head restraint. The manikin assembly may further include load cells for measuring the forces acting on the manikin assembly and accelerometers for measuring the acceleration/deceleration of the manikin assembly.

In one embodiment, the drive member comprises a pendulum having an end pivotally coupled to a frame structure and capable of swinging movement about that end and a decelerator having at least one damper configured to engage the pendulum so as to decelerate the swinging movement of the pendulum. In use, the test assembly, having the head restraint and manikin assembly mounted thereto, is mounted to the pendulum. The pendulum is then moved to a raised position and released. During the swinging movement of the pendulum, the pendulum engages at least one damper near the bottom of its swing, which causes the pendulum to decelerate. The deceleration in turn causes the head and neck portion of the manikin assembly to abruptly move in the rearward direction so that the head portion contacts the head restraint. Dynamic data, such as the imposed forces and accelerations/decelerations of the manikin assembly, may be collected and evaluated to determine the effectiveness of a particular head restraint design concept.

The features and objectives of the present invention will become more readily apparent from the following Detailed Description taken in conjunction with the accompanying drawings.

BRIEF DESCRIPTION OF DRAWINGS

The accompanying drawings, which are incorporated in and constitute a part of this specification, illustrate an embodiment of the invention and, together with a general description of the invention given above, and the detailed description given below, serve to explain the invention.

DETAILED DESCRIPTION

Figure 1:
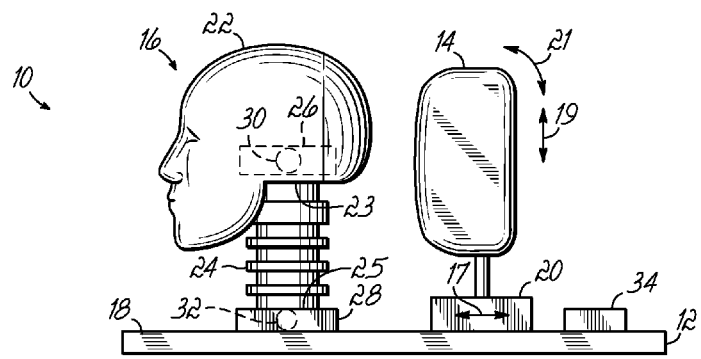
FIG. 1 is a side elevation view of a test assembly according to the invention including a head restraint and a manikin assembly.

With reference to FIG. 1, there is shown a test assembly 10 of the present invention for evaluating head restraint design concepts. Test assembly 10 comprises a carriage 12, a head restraint 14 coupled to carriage 12 and a manikin assembly 16 also coupled to carriage 12 adjacent head restraint 14. Carriage 12 comprises a generally rectangular plate having a top surface 18. A head restraint mounting bracket 20 is coupled to carriage 12 along top surface 18 by means known but not shown. A vehicle head restraint 14 is then coupled to mounting bracket 20. Mounting bracket 20 may be adjustably positioned on carriage 12. For example, head restraint 14 may be moveable in a direction generally parallel to carriage 12 so as to move head restraint 14 toward and away from a head portion 22 of manikin assembly 16, as shown by arrow 17. As shown by arrow 19, head restraint 14 may be further moveable in a direction generally perpendicular to carriage 12 so as to adjust the height of the head restraint 14 relative to head portion 22. Head restraint 14 may also be pivotally coupled to carriage 12, so as to be angularly adjustable as shown by arrow 21, or coupled in other manners depending on the application needs. Manikin assembly 16 is coupled to carriage 12 along top surface 18 by means known but not shown. Manikin assembly 16 comprises head portion 22 coupled to a neck portion 24 at an upper end 23 of neck portion 24. Manikin assembly 16 is coupled to carriage 12 along a lower end 25 of neck portion 24. Head and neck portions 22, 24 are configured to simulate the kinematic response of the human head and neck to motion, such as for example accelerating and/or decelerating motions. As used herein, the term manikin assembly is not to be limited to mechanical devices that simulate the human head and neck, but is broad enough to encompass cadaver head and neck portions. By way of example, federally regulated anthropomorphic test device (ATD) components, such as the Hybrid III head and neck assemblies may be used in the invention. Moreover, adult ATD components as well as child ATD components may be used. It should be noted, however, that the invention is not so limited and any head/neck ATD components may be used in the invention.

To determine the dynamic interacting response of manikin assembly 16 with head restraint 14, manikin assembly 16 may further comprise an upper neck load cell 26 adjacent the upper end 23 of neck assembly 24 and a lower neck load cell 28 adjacent the lower end 25 of neck assembly 24. The upper and lower neck load cells 26, 28 are adapted to measure the rearward and forward shear forces, the tensile and compressive forces and the flexion and extension moments acting on the manikin assembly 16 at load cells 26, 28. Furthermore, manikin assembly 16 may further include accelerometers 30, 32 positioned adjacent the upper end 23 and lower end 25 of neck assembly 24 respectively. Accelerometer 30 is preferably placed at the center of gravity of head portion 22. Accelerometers 30, 32 are adapted to measure the acceleration and/or deceleration of the manikin assembly 16 at accelerometers 30, 32. An accelerometer 34 may further be positioned on carriage 12 to measure the acceleration and/or deceleration of test carriage 12.

To use the test assembly of the present invention to evaluate a particular head restraint design concept, test assembly 10 can be mounted to a drive member that is capable of moving the test assembly. When the drive member is moved, the manikin assembly 16 responds through a corresponding movement of the head and neck portions 22, 24. The motion of the drive surface causes the head portion 22 to contact head restraint 14. The dynamic data, such as that measured by the load cells 26, 28 and accelerometers 30, 32, 34 can be used in evaluating the performance and effectiveness of a particular head restraint design concept.

Figure 2:
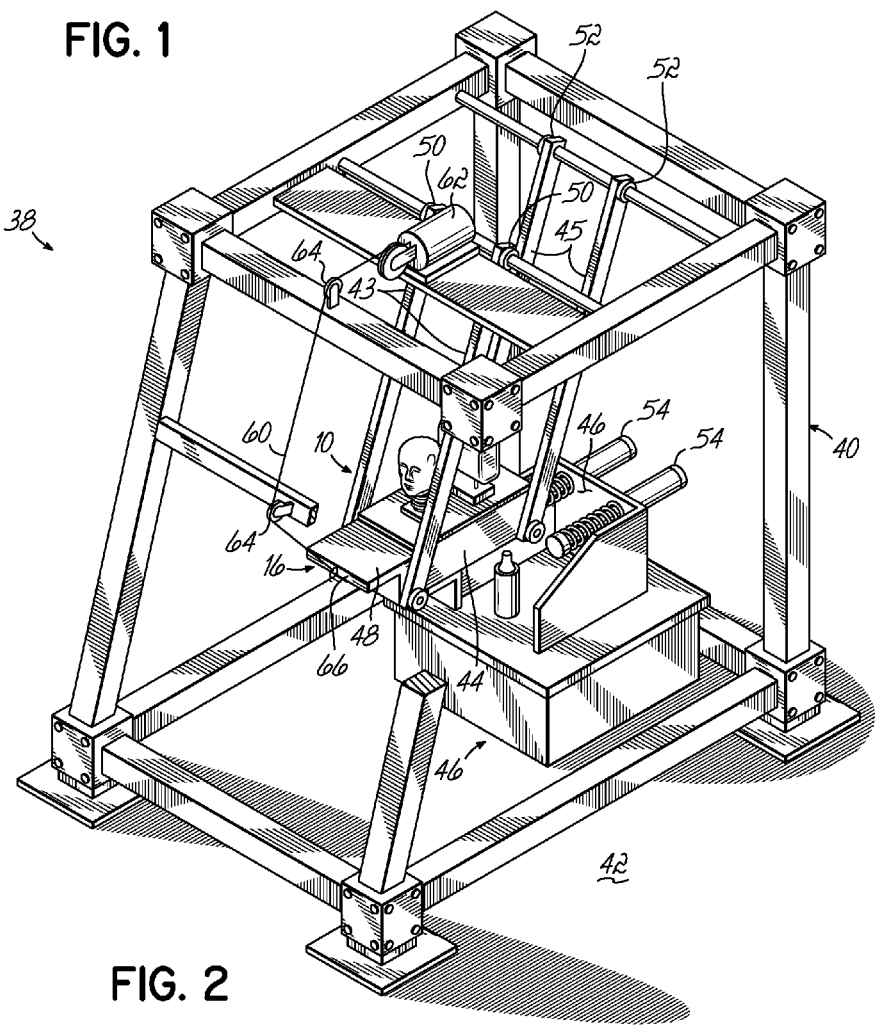
FIG. 2 is a perspective view of a pendulum tester having the test assembly of FIG. 1 mounted thereto.

As shown in FIG. 2, one embodiment of the present invention has test assembly 10 mounted to a pendulum-type tester 38. Pendulum tester 38 includes a frame structure 40 supported on top of a base 42. A pendulum 44 is pivotally connected to frame structure 40 by parallel support arms 43, 45. In this way, pendulum 44 is capable of swinging movement between a raised position and a bottom position. Pendulum tester 38 further includes a decelerator 46 located at the bottom position for engaging the pendulum 44 and decelerating the swinging movement of pendulum 44.

Pendulum 44 comprises a generally planar rectangular surface 48 to which test assembly 10, having the vehicle head restraint 14 and manikin assembly 16 mounted thereto, is coupled by means known but not shown. Support arms 43, 45 have one end pivotally connected to pendulum 44 and the other end pivotally connected to frame structure 40 at pivot joints 50, 52 so that pendulum 44 is capable of swinging movement between a raised position and a bottom position. A decelerator 46 is positioned at the bottom position of the pendulum 44 and supported on base 42. Decelerator 46 comprises a pair of hydraulic dampers 54 for engaging bracket 56, which extends downwardly from the bottom portion 58 of pendulum 44. As will be recognized by those having skill in the art, other types of dampers may be used in the invention, such as, adjustable/non-adjustable pneumatic dampers or energy absorbing materials or structures. As pendulum 44 swings toward the bottom position, bracket 56 engages hydraulic dampers 54 to decelerate the swinging movement of pendulum 44 thereby causing the head portion 22 of manikin assembly 16 to contact head restraint 14. By using different hydraulic dampers 54, the deceleration rate of pendulum 44 may be controlled.

Figure 3:
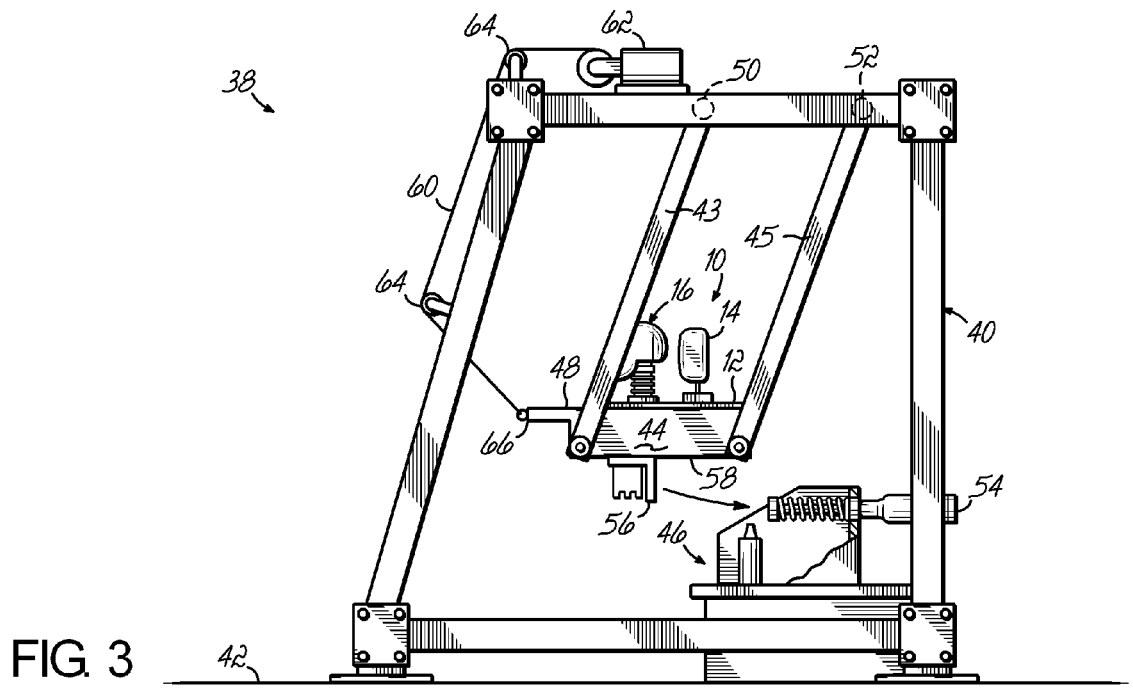
FIG. 3 is a side elevation view of the pendulum tester of FIG. 2 with the pendulum in a raised position.
Figure 4:
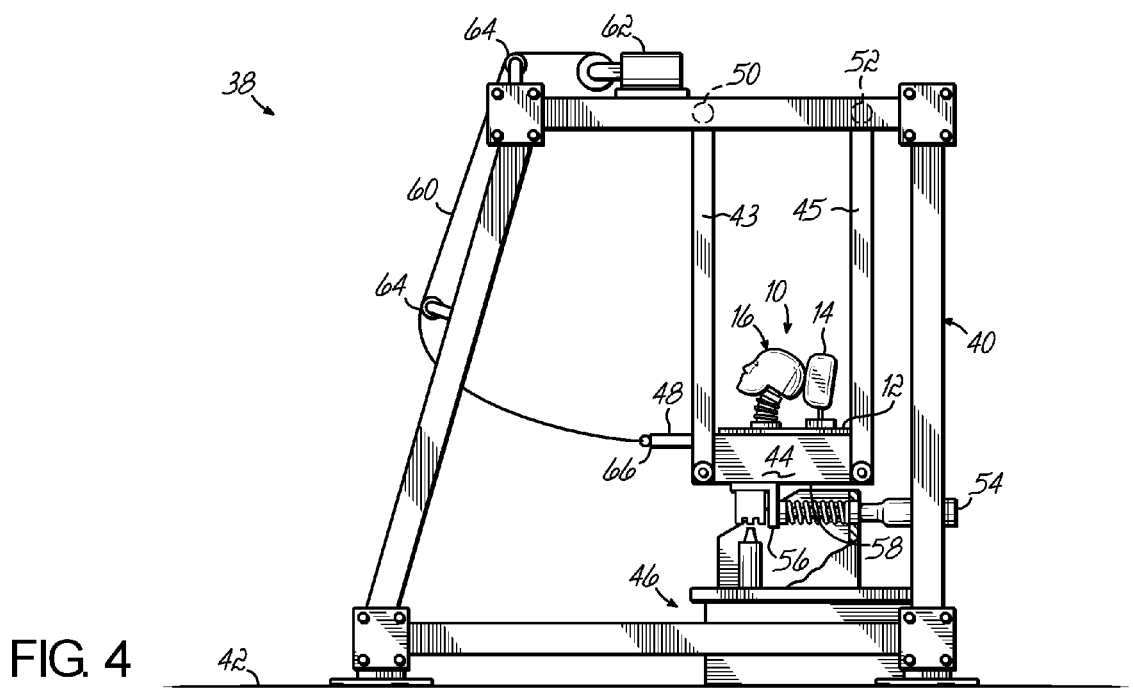
FIG. 4 is a side elevation view of the pendulum tester of FIG. 3 showing the manikin assembly contacting the head restraint due to the deceleration of the pendulum.

Accordingly, and as illustrated in FIGS. 3 and 4, in order to test a particular individual vehicle head restraint using the present invention, the head restraint 14 is mounted in mounting bracket 20, which is coupled to carriage 12. The manikin assembly 16 is then mounted to carriage 12 and carriage 12 is then mounted to pendulum 44. A lift assembly comprising a lift cable 60, winch 62 and pulleys 64 is actuated to raise or swing pendulum 44 to a raised position, as shown in FIG. 3. The raised position of the pendulum 44 may be selectively adjusted for controlling the velocity of the test assembly 10. Lift cable 60 is releasably attached to an end portion 66 of pendulum 44 and is released to allow swinging movement of the pendulum 44 toward the bottom position. Just prior to reaching the bottom position, the bracket 56 engages against dampers 54 thereby decelerating the swinging movement of the pendulum 44. As shown in FIG. 4, this deceleration then causes head and neck portions 22, 24 to move abruptly in the rearward direction so that head portion 22 contacts head restraint 14. Data, such as the force data and the acceleration/deceleration data taken by load cells 26, 28 and accelerometers 30, 32, 34 may be gathered. This data can then be used to evaluate the performance and effectiveness of a particular head restraint design.

It is to be understood that the pendulum tester 38, as herein described, represents but one embodiment of a drive member that may be used in the present invention. Those having skill in the pertinent art will recognize any number of other driven members that may be utilized in accord with the present invention including, but not limited to, an acceleration sled, a deceleration sled or even something as simple as a vertical rail system having gravity-driven motion. It should further be realized that although decelerating motion is used in the described embodiment shown in FIGS. 2–4, the present invention is not so limited and drive members capable of accelerating motions may also be used. The present invention advantageously provides an apparatus and method for evaluating vehicle head restraints under dynamic conditions without the need for performing a test on the overall seat assembly.

It is contemplated that the apparatus and method of the present invention is not a substitute for the traditional sled test, as the sled test is the industry standard and is usually specifically mandated by federal regulations or OEM requirements. Instead, it is contemplated that the apparatus and method of the present invention may be used as a preliminary test to determine the likely response of a particular head restraint design concept during a traditional sled test of the overall seat assembly. With this in mind, and so that a comparison of the data between a test using the present invention and that of the traditional sled test correlate, some of the physical and dynamic parameters of a test using the present invention are determined by the values generally observed in the sled test. For instance, the distance between the manikin assembly 16 and the head restraint 14 on carriage 12 is approximately the same as that used for the sled test. Moreover, the pendulum height and damper resistance are adjusted so that the T1 (base of neck) velocity and acceleration/deceleration measured during a test using the present invention is approximately the same as the T1 velocity and acceleration/deceleration observed in the sled test. By matching some of the physical and dynamic parameters, the present invention produces results that correlate to the results for the head restraint during the sled test of the overall seat assembly. It will be appreciated that other types of test procedures and evaluations may be accomplished with an apparatus of the present invention. For example high speed video may be used in conjunction with conventional photo targets on the carriage 12, head restraint 14, and head portion 22. The photo target on the carriage would be used for reference purposes to determine the movement of head restraint 14 and head portion 22. Also, to determine rotational movement of head portion 22, one photo target would be placed at its center of gravity and another, for example, on the chin area. Using the present invention, a number of head restraint design concepts may be evaluated without the need for testing the overall seat assembly. Typically, after tests using the present invention identify the best performers among the proposed design concepts will a sled test evaluating the overall seat assembly be performed. This results in substantial cost savings and time reduction.

While the present invention has been illustrated by the description of a particular embodiment thereof, and while the embodiment has been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of Applicant's general inventive concept.

What is claimed is:

1. A test assembly for testing vehicle head restraints adapted to be coupled to a drive member capable of moving said test assembly, said test assembly comprising:
   a carriage adapted to be coupled to the drive member;
   a head restraint coupled to said carriage; and
   a manikin assembly coupled to said carriage comprising:
      a head portion; and
      a neck portion having an upper and lower end, said head portion coupled to said upper end of said neck portion, said manikin assembly coupled to said carriage at said lower end of said neck portion,
   wherein said head restraint is positioned adjacent said manikin assembly so that movement of said drive member causes said head portion of said manikin assembly to contact said head restraint.

2. The assembly of claim 1 wherein said manikin assembly further comprises at least one load cell for measuring a force acting on at least a portion of said manikin assembly.

3. The assembly of claim 1 wherein said manikin assembly further comprises at least one accelerometer for measuring at least one of an acceleration and deceleration of at least a portion of said manikin assembly.

4. The assembly of claim 1 wherein a load cell is positioned at the upper and lower ends of said neck portion and an accelerometer is positioned at the upper and lower ends of said neck portion.

5. The assembly of claim 1 wherein said carriage further comprises at least one accelerometer for measuring at least one of an acceleration and deceleration of the carriage.

6. The assembly of claim 1 further comprising a mounting bracket coupled to said carriage, said head restraint coupled to said mounting bracket.

7. The assembly of claim 1 wherein said head restraint is adjustable relative to said carriage.

8. The assembly of claim 7 wherein said head restraint is moveable in a direction generally parallel to said carriage.

9. The assembly of claim 7 wherein said head restraint is moveable in a direction generally perpendicular to said carriage.

10. The assembly of claim 7 wherein said head restraint is angularly adjustable relative to said carriage.

11. An apparatus for testing vehicle head restraints comprising:
   a drive member capable of movement; and
   a test assembly comprising:
      a carriage adapted to be coupled to said drive member;
      a head restraint coupled to said carriage; and
      a manikin assembly coupled to said carriage comprising:
         a head portion; and
         a neck portion having an upper and lower end, said head portion coupled to said upper end of said neck portion, said manikin assembly coupled to said carriage at said lower end of said neck portion,
      wherein said head restraint is positioned adjacent said manikin assembly so that movement of said drive member causes said head portion of said manikin assembly to contact said head restraint.

12. The apparatus of claim 11 wherein said manikin assembly further comprises at least one load cell for measuring a force acting on at least a portion of said manikin assembly.

13. The apparatus of claim 11 wherein said manikin assembly further comprises at least one accelerometer for measuring at least one of an acceleration and deceleration of at least a portion of said manikin assembly.

14. The apparatus of claim 11 wherein a load cell is positioned at the upper and lower ends of said neck portion and an accelerometer is positioned at the upper and lower ends of said neck portion.

15. The apparatus of claim 11 wherein said drive member comprises:
   a pendulum having an end pivotally coupled to a frame structure and capable of swinging movement about said end; and
   a decelerator including at least one damper for engaging said pendulum and decelerating the swinging movement of said pendulum.

16. A method of testing a vehicle head restraint using a manikin assembly comprising a head portion and a neck portion having an upper and lower end, the head portion coupled to the upper end of the neck portion, the method comprising:
    mounting the head restraint to a drive member;
    mounting the manikin assembly to the drive member at the lower end of the neck assembly; and
    moving the drive member; and
    causing the head portion of the manikin assembly to contact the head restraint.

17. The method of claim 16 wherein causing the head portion of the manikin assembly to contact the head restraint comprises accelerating the drive member so that the head portion of the manikin assembly contacts the head restraint.

18. The method of claim 16 wherein causing the head portion of the manikin assembly to contact the head restraint comprises decelerating the drive member so that the head portion of the manikin assembly contacts the head restraint.

19. The method of claim 16 further comprising measuring a force acting on at least a portion of the manikin assembly.

20. The method of claim 16 further comprising measuring at least one of an acceleration and deceleration of at least a portion of the manikin assembly.

21. The method of claim 16 wherein mounting the head restraint and the manikin assembly to a drive member comprises mounting the head restraint and manikin assembly to a pendulum.

22. The method of claim 21 wherein moving the drive member comprises:
    positioning the pendulum in a raised position; and
    releasing the pendulum.

23. The method of claim 21 wherein causing the head portion of the manikin assembly to contact the head restraint comprises:
    engaging the pendulum with at least one damper; and
    decelerating the swinging movement of the pendulum.

24. A method of testing a vehicle head restraint using a manikin assembly comprising a head portion and a neck portion having an upper and lower end, the head portion coupled to the upper end of the neck portion, the method comprising:
    mounting the head restraint to a carrier;
    mounting the manikin assembly to the carrier at the lower end of the neck assembly;
    mounting the carrier to a pendulum;
    positioning the pendulum in a raised position;
    releasing the pendulum;
    engaging the pendulum with at least one damper;
    decelerating the swinging movement of the pendulum;
    causing the head portion of the manikin assembly to contact the head restraint.

* * * * *